United States Patent
Shan et al.

(10) Patent No.: US 6,605,100 B1
(45) Date of Patent: Aug. 12, 2003

(54) SCALPEL BLADE EXCHANGE APPARATUS AND METHOD

(76) Inventors: Yansong Shan, 300 Glenwood, Apt. 109, Monterrey, CA (US) 93940; Lelia Yu, 300 Glenwood, Apt. 109, Monterrey, CA (US) 93940

(*) Notice: Subject to any disclaimer, the term of this patent is extended or adjusted under 35 U.S.C. 154(b) by 0 days.

(21) Appl. No.: 09/856,741
(22) PCT Filed: Nov. 24, 1999
(86) PCT No.: PCT/US99/28036
§ 371 (c)(1),
(2), (4) Date: Sep. 24, 2001
(87) PCT Pub. No.: WO00/32114
PCT Pub. Date: Jun. 8, 2000

Related U.S. Application Data

(60) Provisional application No. 60/109,829, filed on Nov. 25, 1998.

(51) Int. Cl.[7] .......................... A61B 17/32; B65D 83/10
(52) U.S. Cl. ................................. 606/167; 206/355
(58) Field of Search ........................ 606/167; 206/355, 206/352; 30/329, 339, 346

(56) References Cited

U.S. PATENT DOCUMENTS 5,571,127 A * 11/1996 DeCampli .................. 606/167
5,730,751 A * 3/1998 Dillon et al. .............. 606/167

* cited by examiner

Primary Examiner—Michael J. Milano
Assistant Examiner—Gwen Phanijphand
(74) Attorney, Agent, or Firm—James M. Deimen

(57) ABSTRACT

A modified scalpel and blade exchanging apparatus and method whereby insertion of the scalpel blade (106) end into the apparatus and turning of the scalpel handle (111) causes the dull or spent blade to be exchanged with a new blade (130) on the scalpel (101) in a few seconds. The quick exchange is accomplished by a cam system (183, 184) that opens and closes the jaws or fingers (104, 105) that retain the blade on the scalpel and a dispenser (119) that positions the new blade in the open jaws or fingers just prior to closure. The new invention solves the problem of detaching and attaching scalpel blades in a matter of seconds without danger to the user. With a mere twist of the wrist, the user detaches the dull blade and attaches the new blade, the dull blade dropping into a sharps container (107) upon detachment. Also, by the design of the apparatus, contact of the dull contaminated blade with the apparatus is substantially eliminated with the exception of a protective cap (102A), protective ring (340) or disposable socket (102) that are removable for separate sterilization or disposal. In the preferred embodiments, the new blades are dispensed from a cartridge (119) and multiple cartridges may be provided for the selection of differing blades.

11 Claims, 15 Drawing Sheets

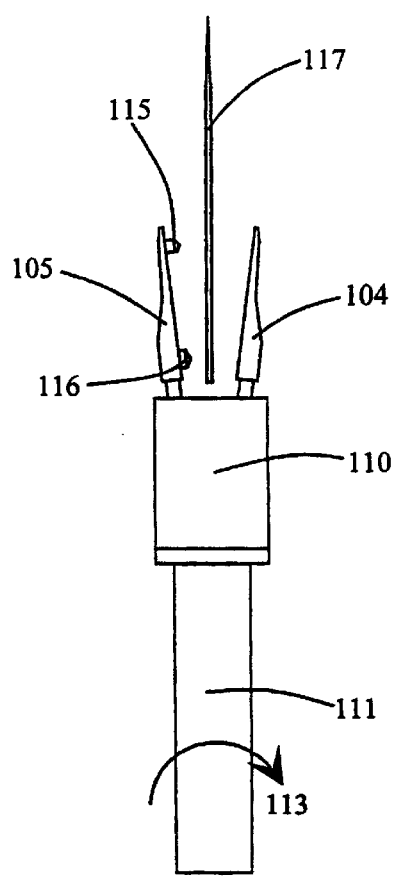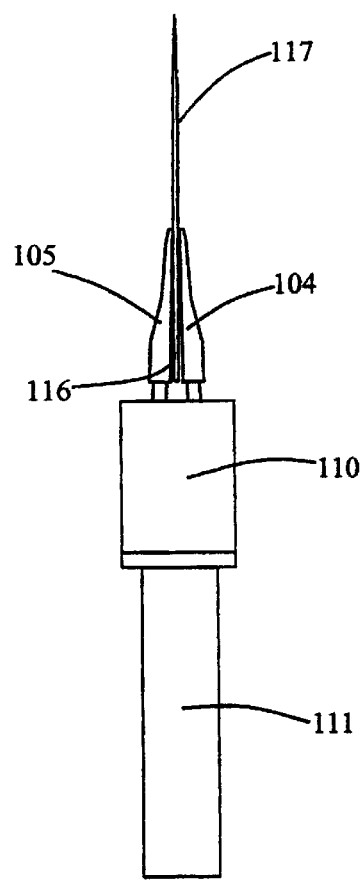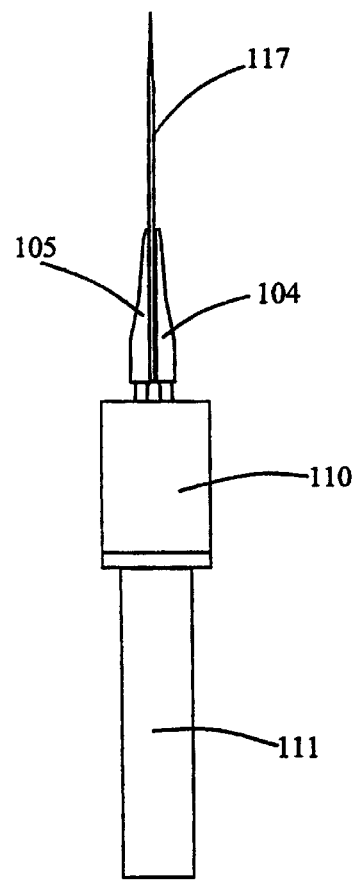
FIG. 4.1  FIG. 4.2  FIG. 4.3
FIG. 4

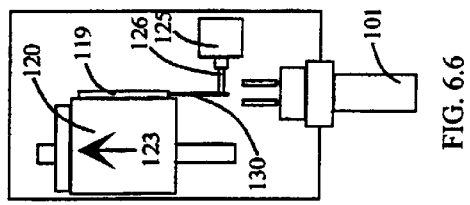
FIG. 6.6
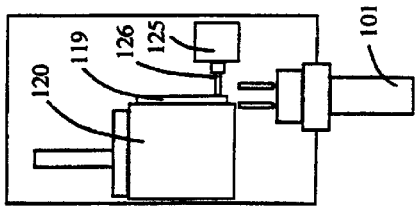
FIG. 6.5
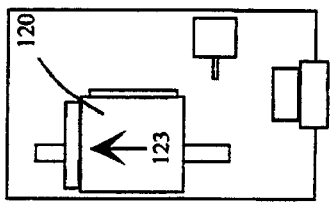
FIG. 6.11
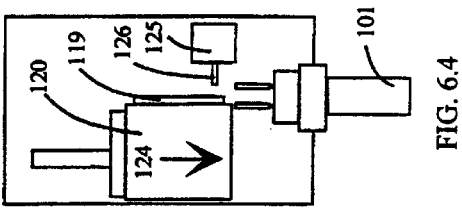
FIG. 6.4
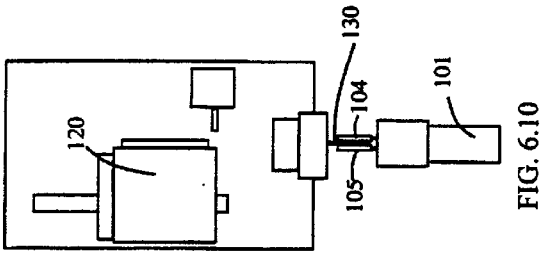
FIG. 6.10
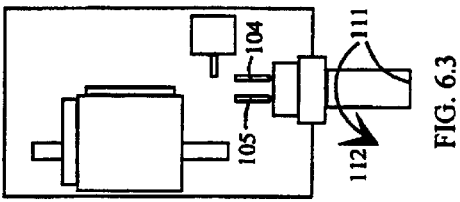
FIG. 6.3
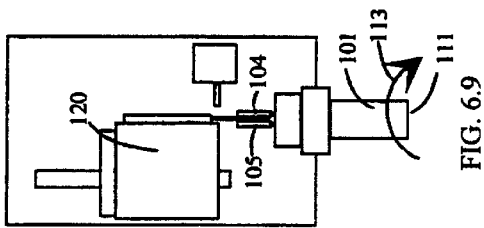
FIG. 6.9
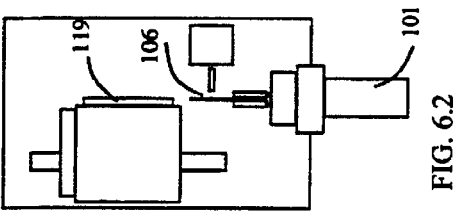
FIG. 6.2
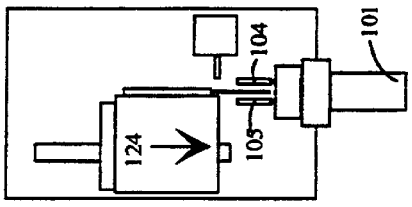
FIG. 6.8
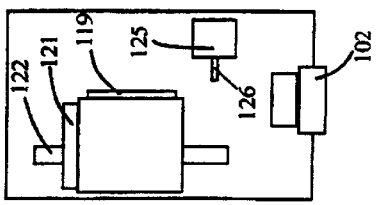
FIG. 6.1
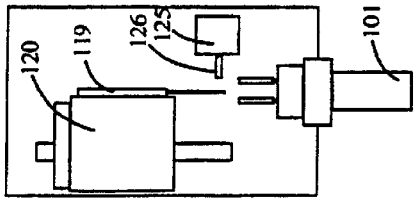
FIG. 6.7
FIG. 6

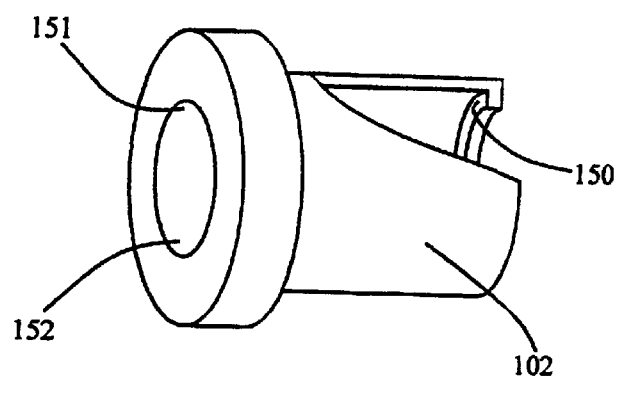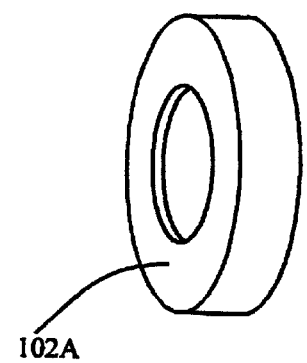
FIG. 7             FIG. 7.1

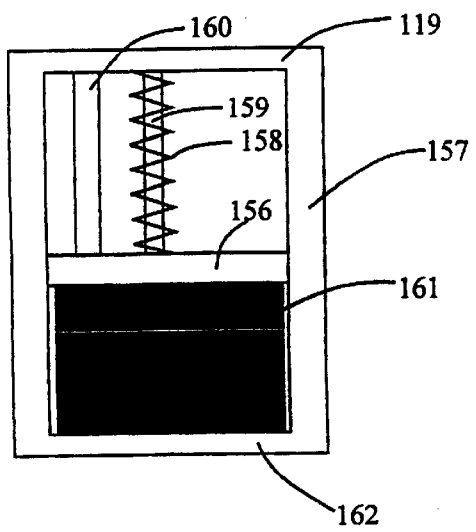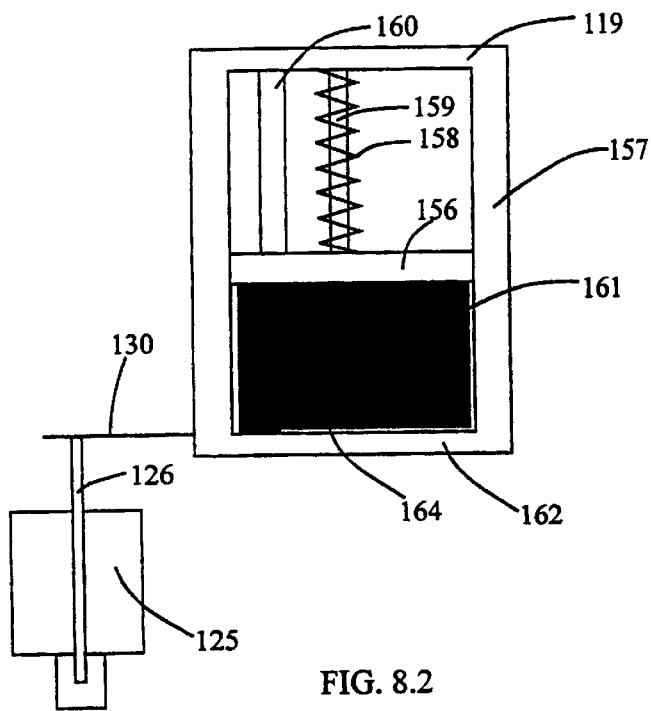
FIG. 8.1  FIG. 8.2
FIG. 8

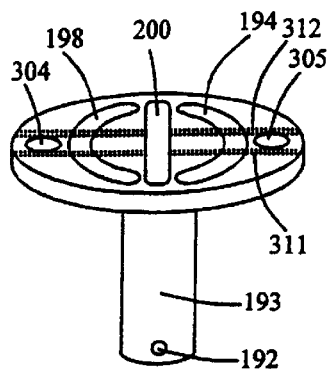
FIG. 10.7
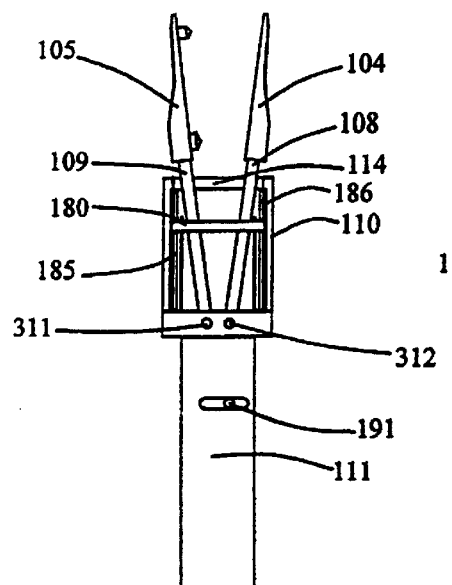
FIG. 10.1.a   FIG. 10.1.b
FIG. 10.1
FIG. 10.6
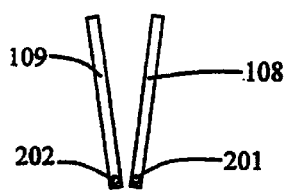
FIG. 10.8
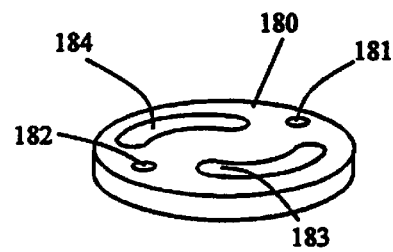
FIG. 10.3
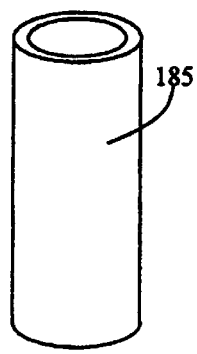
FIG. 10.5
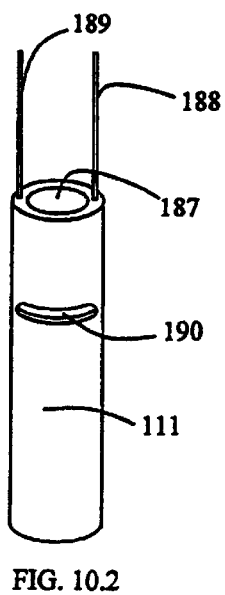
FIG. 10.2
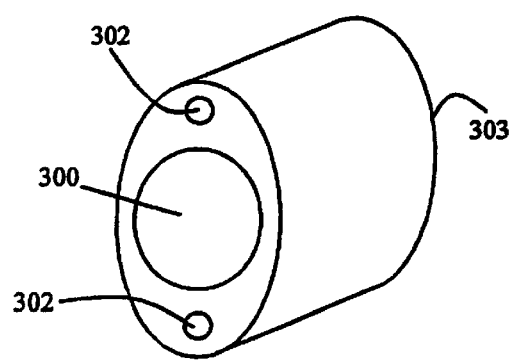
FIG. 10.4
FIG. 10

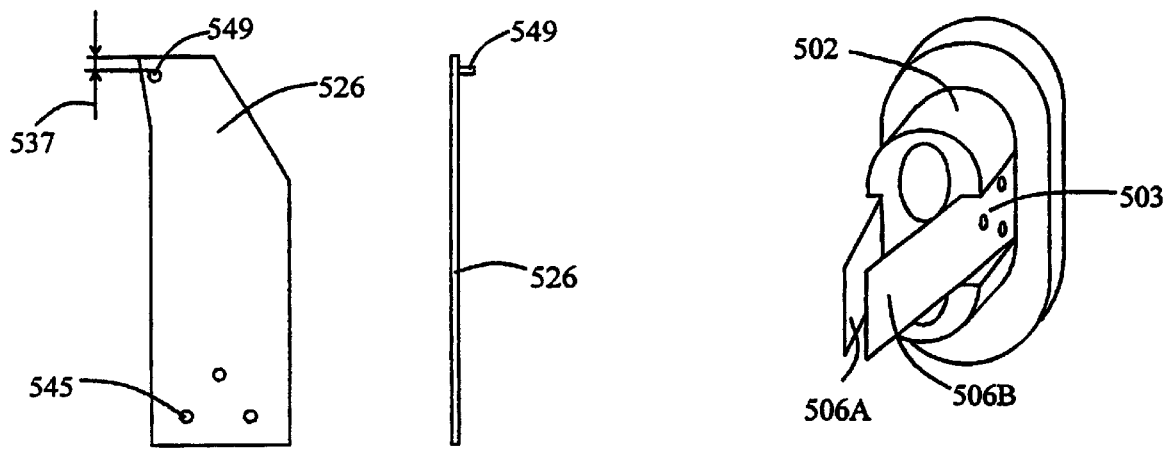
FIG. 15A    FIG. 15B    FIG. 16
FIG. 15
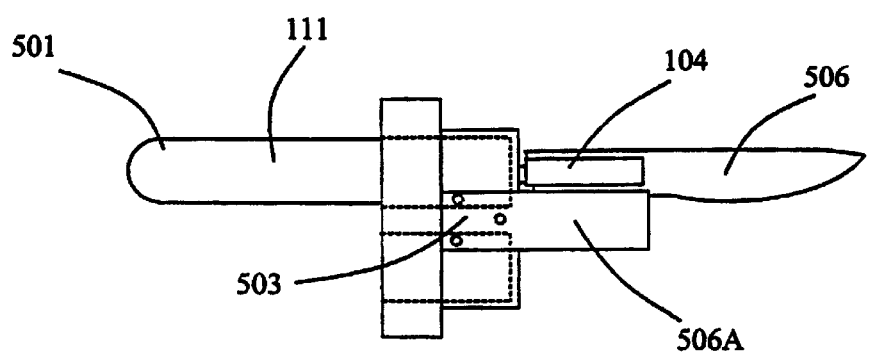
FIG. 17

SCALPEL BLADE EXCHANGE APPARATUS AND METHOD

This application claims the benefit of Provisional Application No. 60/109,829 filed Nov. 25, 1998.

BACKGROUND OF THE INVENTION

The field of the invention pertains to medical scalpels and, in particular, safe methods and apparatus for replacing the scalpel blade.

The typical medical scalpel blade is extremely sharp and held very rigidly in the scalpel handle. Even after too dull for continued use, the blade is extremely sharp and therefore potentially dangerous when manually removed from the scalpel handle for replacement. Moreover, in pathology laboratories, in particular, the dull blade may be contaminated with a variety of unknown, but very dangerous, pathogens such as hepatitis varieties, human immunodeficiency virus (HIV), and tetanus.

The scalpels are widely used in hospitals, laboratories and numerous industrial sectors. In a typical application, a scalpel blade is discarded after several uses and a new blade installed onto the scalpel handle. Because of the possible contamination with pathogens, the manual process of removing the dull blade from the scalpel handle is fraught with risk. U.S. Pat. No. 4,903,390 reveals a device wherein a scalpel user can insert a scalpel in a "box" containing a mechanism. The user maneuvers the scalpel in a specified way and the blade is detached from the handle. This device is only directed to removal of the dull scalpel blade. Attachment of a new blade to the scalpel handle is not addressed.

With a view toward substantially eliminating the hazards associated with exchanging blades on a scalpel, the following apparatus and method has been developed.

SUMMARY OF THE INVENTION

The purpose of the new invention is to eliminate the danger involved in changing scalpel blades and to increase user working efficiency.

The invention comprises a modified scalpel and a blade exchanging apparatus and method whereby insertion of the scalpel blade end into the apparatus causes the dull blade to be exchanged with a new blade on the scalpel in a few seconds.

The quick exchange is accomplished by a cam system that opens and closes the jaws or fingers that retain the blade on the scalpel and a dispenser that positions the new blade in the open jaws or fingers just prior to closure.

The new invention solves the problem of detaching and attaching scalpel blades in a matter of seconds without danger to the user. With a mere twist of the wrist, the user detaches the dull blade and attaches the new blade. Also, by the design of the apparatus, contact of the dull contaminated blade with the apparatus is substantially eliminated with the exception of a "protective ring" that is removable for separate sterilization. The protective ring minimizes the likelihood of inadvertent contact of the dull blade with the apparatus. In normal use, the dull blade need not contact the apparatus, the dull blade being allowed to merely fall into a sharps container upon turning of the scalpel handle thereby opening the scalpel jaws or fingers.

BRIEF DESCRIPTION OF THE DRAWINGS

FIG. 4 illustrates the steps in attaching a new blade to the scalpel;

FIG. 6 illustrates in sequence the process of replacing a used blade with a new blade;

FIG. 7 is a cutaway view of the scalpel positioning socket of the apparatus;

FIG. 8 illustrates in sequence and in plan view the cartridge structure and operation;

FIG. 10 illustrates the parts and the mechanism in the scalpel handle;

FIGS. 15a and 15b are side and edge views of an alternative form of a blade extraction pin;

FIG. 16 is a perspective internal view of a dual socket for the dual blade exchange apparatus of FIG. 13; and FIG. 17 is a side view of the dual socket of FIG. 16 with a scalpel therein.

DESCRIPTION OF THE PREFERRED EMBODIMENT

Figure 1:
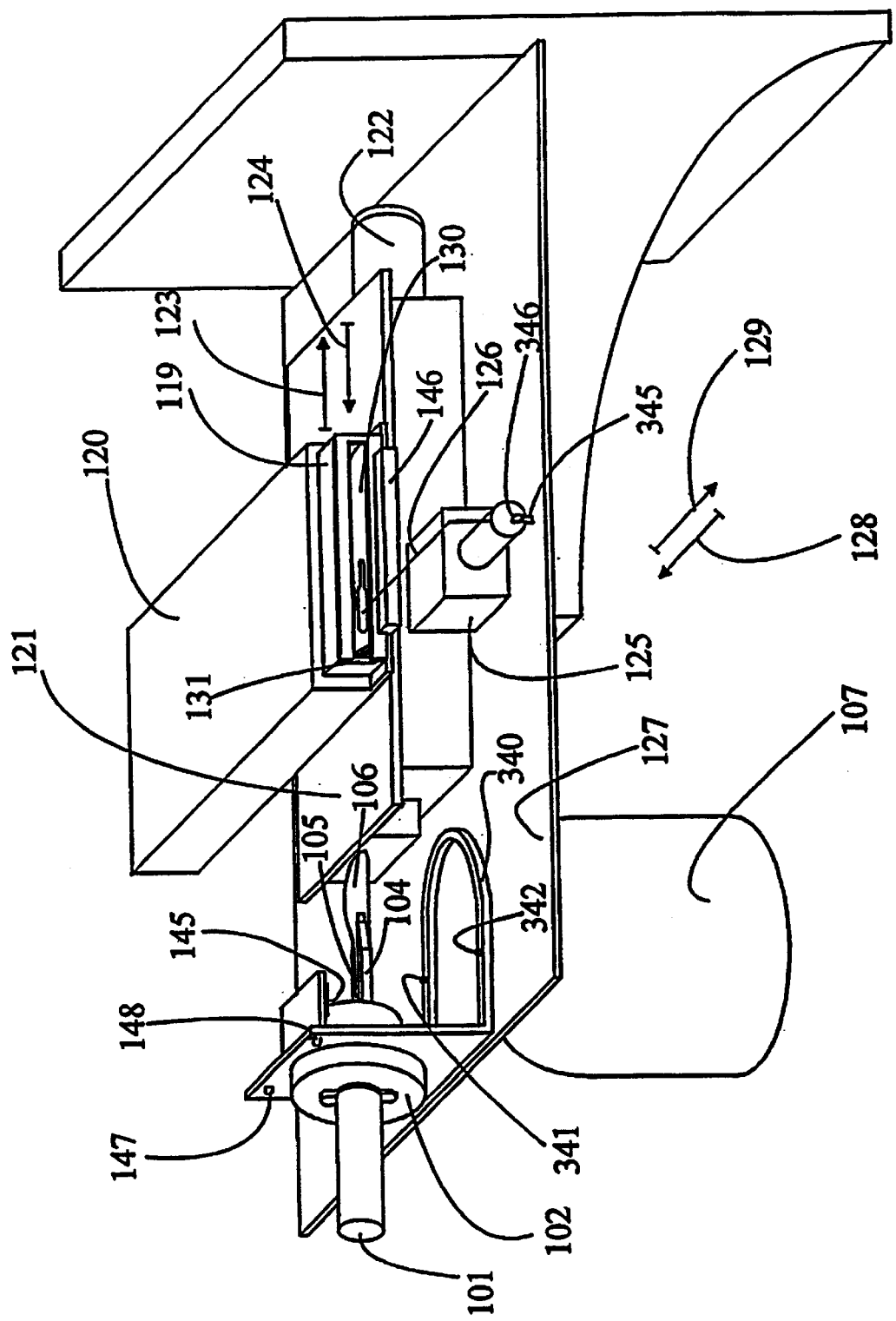
FIG. 1 illustrates in perspective the apparatus with the protective cover removed.

In FIG. 1 the scalpel 101 is inserted with the scalpel handle extending from the inlet positioning socket 102. The inlet positioning socket 102 only allows insertion in a particular orientation so that the clamping fingers 104 and 105 of the scalpel 101 can only be opened or closed in a horizontal direction. The inlet positioning socket 102 also limits the depth of scalpel insertion so that upon opening of the clamping fingers 104 and 105 the dull used blade 106 drops precisely into a sharps container 107 attached therebelow.

Figure 2:
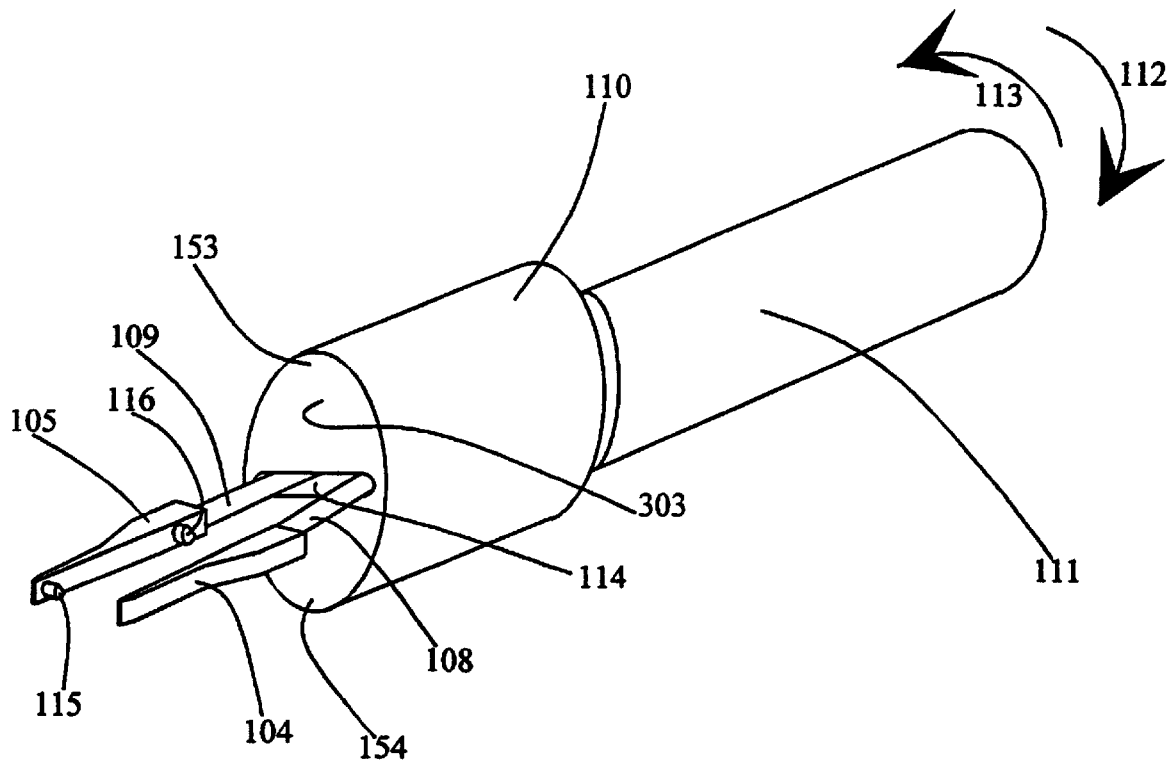
FIG. 2 illustrates in perspective the scalpel.

In FIG. 2 as shown, the clamping fingers 104 and 105 can be opened or closed by moving the two arms 108 and 109 attached to the respective clamping fingers. The two arms 108 and 109 are constrained to move in the slot 114. The motion of the two arms 108 and 109 is controlled by twisting the scalpel handle 111 relative to the scalpel frame 110. The internal mechanism of the scalpel 101 is further discussed below with respect to FIG. 10.

Figure 3:
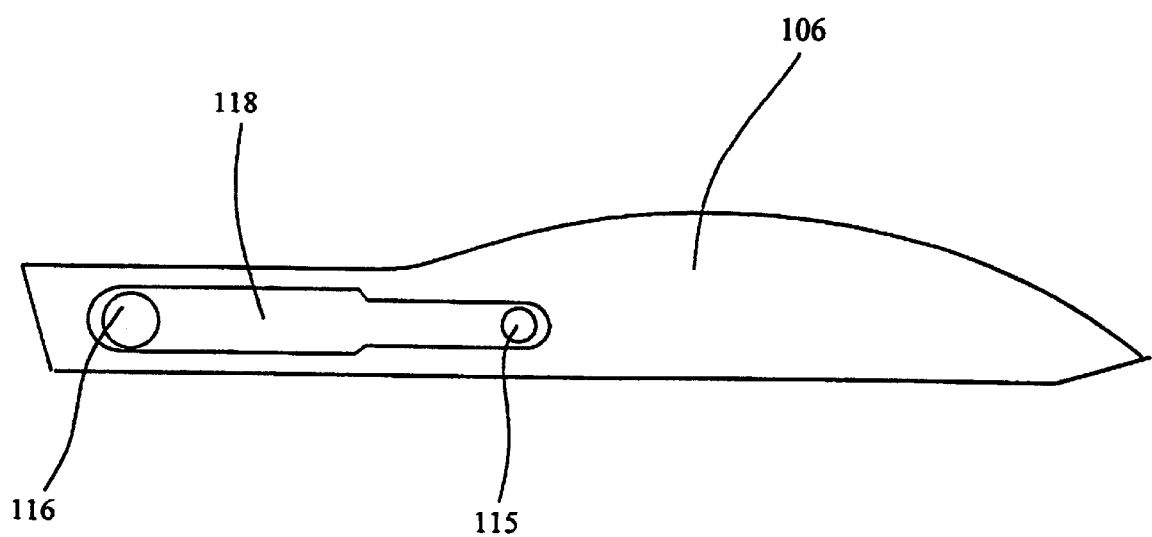
FIG. 3 illustrates in side view a scalpel blade.

When the scalpel handle 111 is turned in the direction of arrow 112, the clamping fingers 104 and 105 open and the dull used blade drops into the sharps container 107. When a new blade is positioned between the clamping fingers 104 and 105 as discussed below, by turning the scalpel handle 111 in the direction of arrow 113 the clamping fingers will clamp the fresh blade therebetween. Finger 105 is formed with two short pins 115 and 116 as shown in FIG. 2. These short pins 115 and 116 fit through the slot 118 of blade 106, as best shown in FIG. 3 to secure the position of the blade in the clamped fingers 104 and 105.

FIG. 4 shows the process of clamping a new blade 117 onto the scalpel 101. First, as discussed further below, the apparatus places the new blade in position between the clamping fingers 104 and 105. Upon turning the handle 111 in the direction of arrow 113, the two clamping fingers 104 and 105 close in a manner that assures full tightness on the blade 117 at the tips of the fingers. Closure is shown in the sequence of FIGS. 4.1, 4.2 and 4.3 wherein from FIG. 4.1 with the fingers 104 and 105 fully open and the pins 115 and 116 showing, the fingers first close to FIG. 4.2 wherein the tips of the fingers are shown tighter to the blade 117 than the balance of the fingers. A final slight twist to the handle 111 causes the fingers 104 and 105 to fully clamp the blade 117 as shown in FIG. 4.3.

Figure 5:
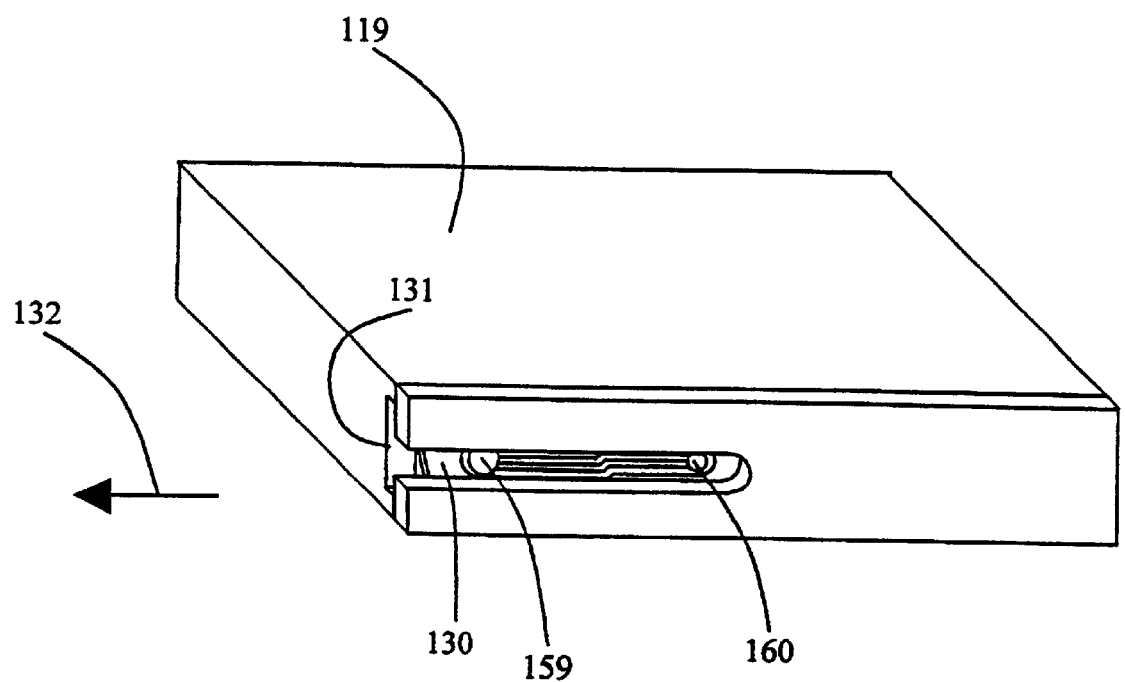
FIG. 5 illustrates in perspective the scalpel blade dispenser cartridge.

As shown in FIGS. 1 and 5, new blades 130 are dispensed from a cartridge 119 placed in a cartridge box 120. The cartridge box 120 is fixed to a sliding table 121 in turn actuated to reciprocate by a motor 122. The motor 122 is controlled electrically by a computer based motor controller for motion of the table 121 in backward direction 123 and forward direction 124.

An electromagnetic solenoid 125 is attached to the apparatus base 127 just below the open end of the cartridge box 120 and cartridge 119. An L-shaped pin 126 is attached to the solenoid plunger for movement therewith in directions shown by arrows 128 and 129 transverse to the movement of the table 121. Under computer control when the solenoid is moved in direction 128, the pin 126 is inserted into the slot in the stack of new blades in the cartridge 119. However, the pin 126 only reaches into the slot of the first blade. A key 345 is fixed to the base 127 of the apparatus. The key 345 engages a slot 346 in the solenoid plunger to prevent rotation of the plunger and misalignment of the pin 126.

The opening 131 in the cartridge 119 is sized to only permit one blade to exit the cartridge through the opening in the relative direction 132. Thus, after pin 126 is inserted into the next blade 130 in the cartridge 119, movement of the sliding table 121 in direction 123 pulls the next blade from the cartridge 119.

The step-by-step process for replacing a dull used blade with a new blade is illustrated in FIG. 6. FIG. 6.1 shows the new apparatus absent the insertion of a scalpel. Upon insertion of a scalpel 101 with a used dull blade 106 therein as shown in FIG. 6.2 the handle 111 is rotated (arrow 112) to open the clamping fingers 104 and 105 as shown in FIG. 6.3 and cause the old blade to be discarded as discussed above.

Next, as shown in FIG. 6.4, the cartridge box 120 and cartridge 119 move toward the scalpel 101 and into alignment with pin 126. Pin 126 extends into the next new blade 130 in the cartridge 119 in FIG. 6.5 and the cartridge box 120 and cartridge 119 retract as shown by arrow 123 in FIG. 6.6 leaving the new blade extended from the cartridge. The solenoid 125 retracts the pin 126 in FIG. 6.7 leaving the new blade 130 extended, and in FIG. 6.8 the cartridge 119 and cartridge box 120 move (arrow 124) toward the scalpel 101 thereby positioning the new blade 130 properly between the clamping fingers 104 and 105.

The handle 111 of the scalpel 101 is rotated back 113 to close the fingers 104 and 105 and clamp the new blade 130 as shown in FIG. 6.9 and the scalpel can be withdrawn from the apparatus as shown in FIG. 6.10. The cartridge box 120 then returns to standby position as shown in FIG. 6.11. The entire sequence of FIG. 6 takes only a matter of seconds for the complete cycle avoiding any contact by the user with the dull used blade or new blade in the blade exchange process.

As shown in FIG. 1, a non-contact photo-electric sensor 145 detects the opening or closing of the clamping fingers 104 and 105. Sensor 145 constantly emits a light beam that is reflected only when clamping finger 104 is directly thereunder. The receiver in sensor 145 senses the reflected light and signals the computer that an open scalpel is in place in the apparatus.

During the entire blade change process, the open scalpel fingers 104 and 105 are sensed by sensor 145 in FIG. 6.3 beginning the sequence of steps shown in FIGS. 6.4 through 6.9. In FIG. 6.10, the sensor 145 senses closure of the clamping fingers 104 and 105, and the computer causes the cartridge 119 and cartridge box 120 to retract in FIG. 11.

Two light emitting diode (LED) lights 147 and 148 indicate to the user the working status of the apparatus. LED 147 is a green light that indicates the apparatus is ready for the user to insert a scalpel into the socket 102. Upon rotating the scalpel handle 111, LED 148 lights in yellow indicating to the user that the apparatus is executing the series of steps to exchange a blade and that the user should not extract the scalpel from the apparatus. When the green LED light 147 returns, after the sequence of steps through FIG. 6.9, the user can safely remove the scalpel in the step of FIG. 6.10.

In FIG. 7, inlet positioning socket 102 comprises an elliptical bore having opposed maxima 151 and 152 that engage a pair of complementary maxima 153 and 154 on the scalpel frame 110 shown in FIG. 2. The scalpel frame 110 therefore is prevented from rotating when the scalpel is in the apparatus and, the handle 111 is rotated to open or close the clamping fingers 104 and 105. The socket 102 is also formed with a stop at 150 to limit the insertion of the scalpel into the apparatus. Therefore, the scalpel socket 102 precisely positions the scalpel in the apparatus during the blade exchanging process. The socket 102 may be made a separately disposable or sterilizable item in the event the socket is contaminated by a blade or scalpel frame.

FIGS. 8.1 and 8.2 show the internal structure of the cartridge 119. Inside the cartridge frame 157, a spring 158 urges the blades 161 up against the front panel 162. The spring 158 acts upon a block 156 which contacts the last blade in the cartridge blade stack. Two pins 159 and 160 align the blade stack, block 156 and spring 158. Both pins 159 and 160 terminate at the blade 164 second to the blade to be dispensed next as best illustrated in FIG. 8.2. Therefore, the blade 130 being dispensed can pass by the pins 159 and 160 which are in the blade slots of the blades 161 remaining in the cartridge as also shown in FIG. 5.

Figure 9:
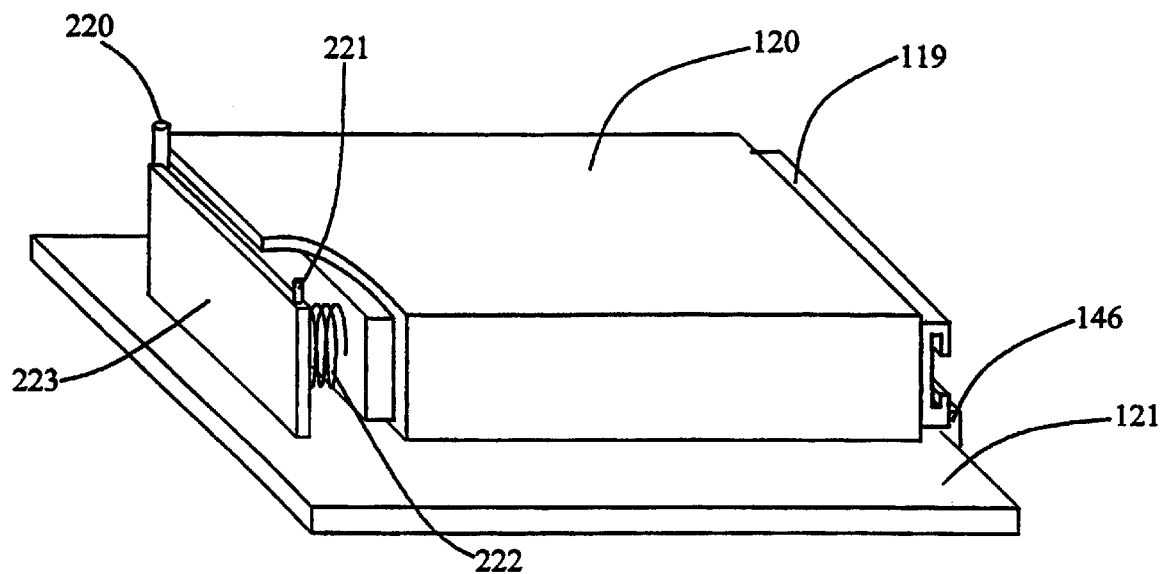
FIG. 9 is a cutaway view of the cartridge box and cartridge in the apparatus.

In FIG. 9 the cartridge 119 in the cartridge box 120 are shown on the table 121. The inner dimensions of the cartridge box 120 are sized to only permit convenient sliding of the cartridge 119 in and out of the box when replacing a spent cartridge. A stop 146 positions the cartridge 119 inside the box 120 for proper alignment of the new blade to be dispensed as also shown in FIG. 1. After a cartridge 119 is manually inserted into the box 120 and against the stop 146 a door 223 with a hinge 220 connection to the box 120 may be closed and latched with a pin 221 trapping a spring 222 between the door and the cartridge to retain the cartridge against the stop 146.

In FIG. 10 the components and structure of the scalpel 101 are illustrated. FIG. 10.1 illustrates in perpendicular partial cross-sections the mechanism principally inside the frame 110 of the scalpel. As shown above, the clamping fingers 104 and 105 extend from clamping arms 108 and 109 which, in turn, extend down into the frame 110.

The handle 111, also shown in FIG. 10.2, has two pins 188 and 189 affixed thereto and extending inside the frame 110. The handle 111 also includes an axial bore 187 extending inward at least beyond the slot 190. Pins 188 and 189 extend through holes 181 and 182 in driving disk 180 shown in FIG. 10.3. The driving disk 180 is thereby caused to rotate with the handle 111 relative to the frame 110 (see arrows 112 and 113 in FIG. 2). Formed in the driving disk 180 are a pair of cam slots 183 and 184.

Frame 110 illustrated in FIG. 10.4 is formed with a cylindrical bore 300 terminating with a solid covered panel 303 having the slot 114 formed in the panel as also shown in FIG. 2. The driving disk 180 is axially located inside the frame 110 by a pair of tubes 185 and 186 illustrated in FIGS. 10.5 and 10.6. The axial location is best shown in FIG. 10.1.

The base 193 of the frame 110 is illustrated in FIG. 10.7 wherein the upper part is formed with two screw holes 304 and 305 that match threaded holes 301 and 302 of the frame 110 (see FIG. 10.4) for attachment with screws 306 and 307 as shown in FIG. 10.1. The base 193 upper part is formed with two arcuate slots 194 and 198 through which pass the pins 188 and 189 and which allow the relative motion of the pins 188 and 189.

The clamping arms 108 and 109 are shown in FIG. 10.8 having holes 201 and 202 therethrough for short pins 311 and 312 to pass through. These pins 311 and 312 rotatably affix the clamping arms 108 and 109 to the base 193 just below the slot 200. Pin 191 tightly fits in hole 192 of base 193 and extends into slot 190 of the handle 111. Thus, handle 111 is constrained to rotatable motion relative to frame 110 without axial movement. Since the clamping arms 108 and 109 pass through the slot 200 in the base 193 and the slot 114 in the frame 110, they are constrained to move in a single axial plane. However, the combination of the separation distance of the pins 311 and 312 and the shape of the cam slots 183 and 184 through which the clamping arms 108 and 109 also pass forces the tips of the clamping fingers 104 and 105 to first contact as shown in FIG. 4.2 when the handle 111 is rotated to close (arrow 113).

Returning to FIGS. 1 and 7, FIG. 7.1 illustrates an optional snap-on protective cap 102A for the outside of socket 102. The protective cap is of throw-away plastic or sterilizeable metal and easily replaceable. The protective cap 102A intercepts inadvertent contact of the used dull and contaminated blade with the outside of the socket 102 thereby greatly reducing the likelihood of contamination of the apparatus. The new apparatus provides exchange of scalpel blades without contact of the blades and therefore under exceptionally sterile conditions.

A protective ring 340 may also be installed with screws 341 and 342 to protect against dull blades that do not fall directly into the sharps container 107. This ring 340 may also be either sterilizeable or throw-away.

Figure 11:
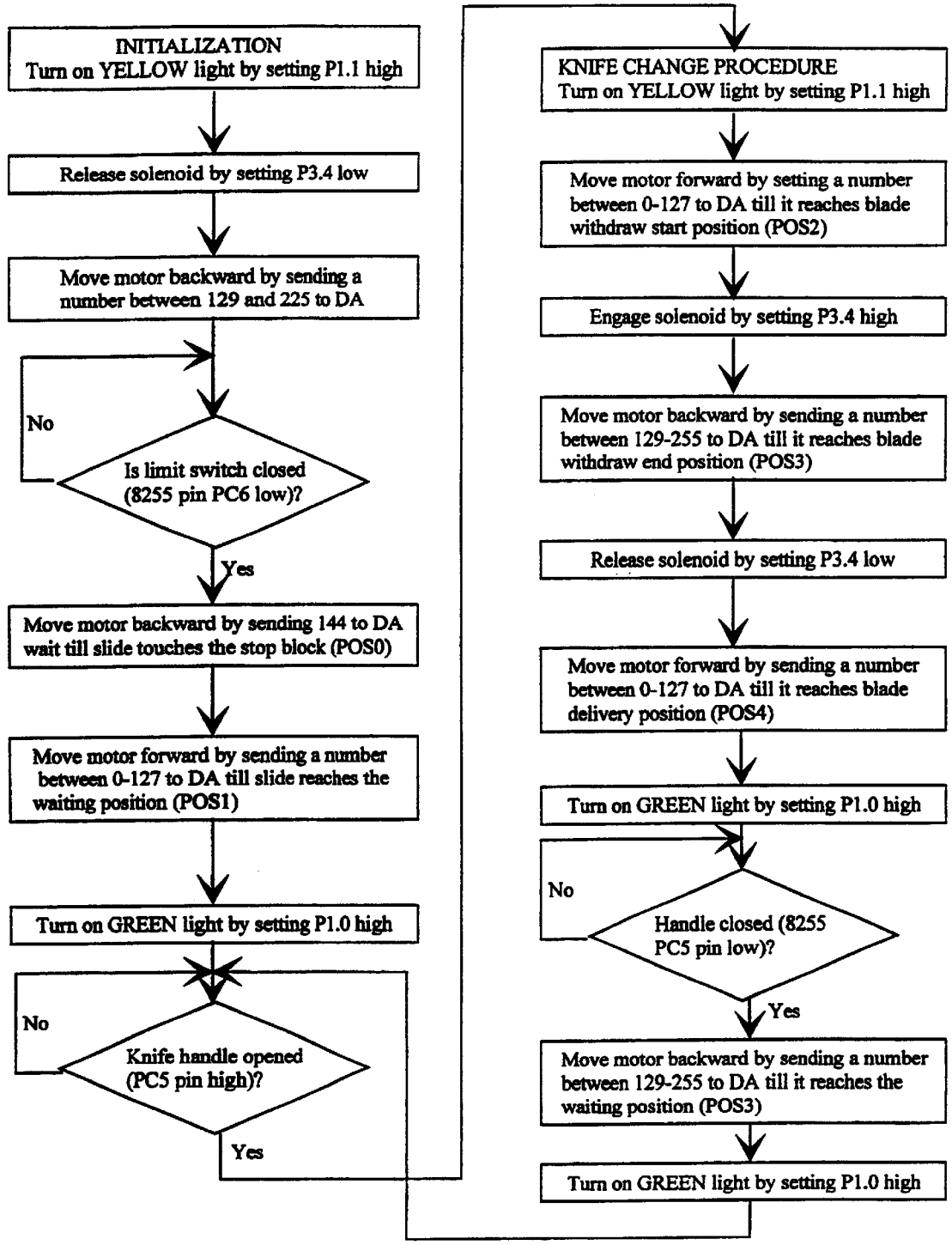
FIG. 11 is a flow chart of the software for controlling the apparatus.

FIG. 11 illustrates a flow diagram for the microprocessor control of the process and apparatus. In prototype testing, blade exchange is accomplished by a mere "twist of the wrist" for a few seconds while the yellow light is observed on the apparatus.

Figure 12:
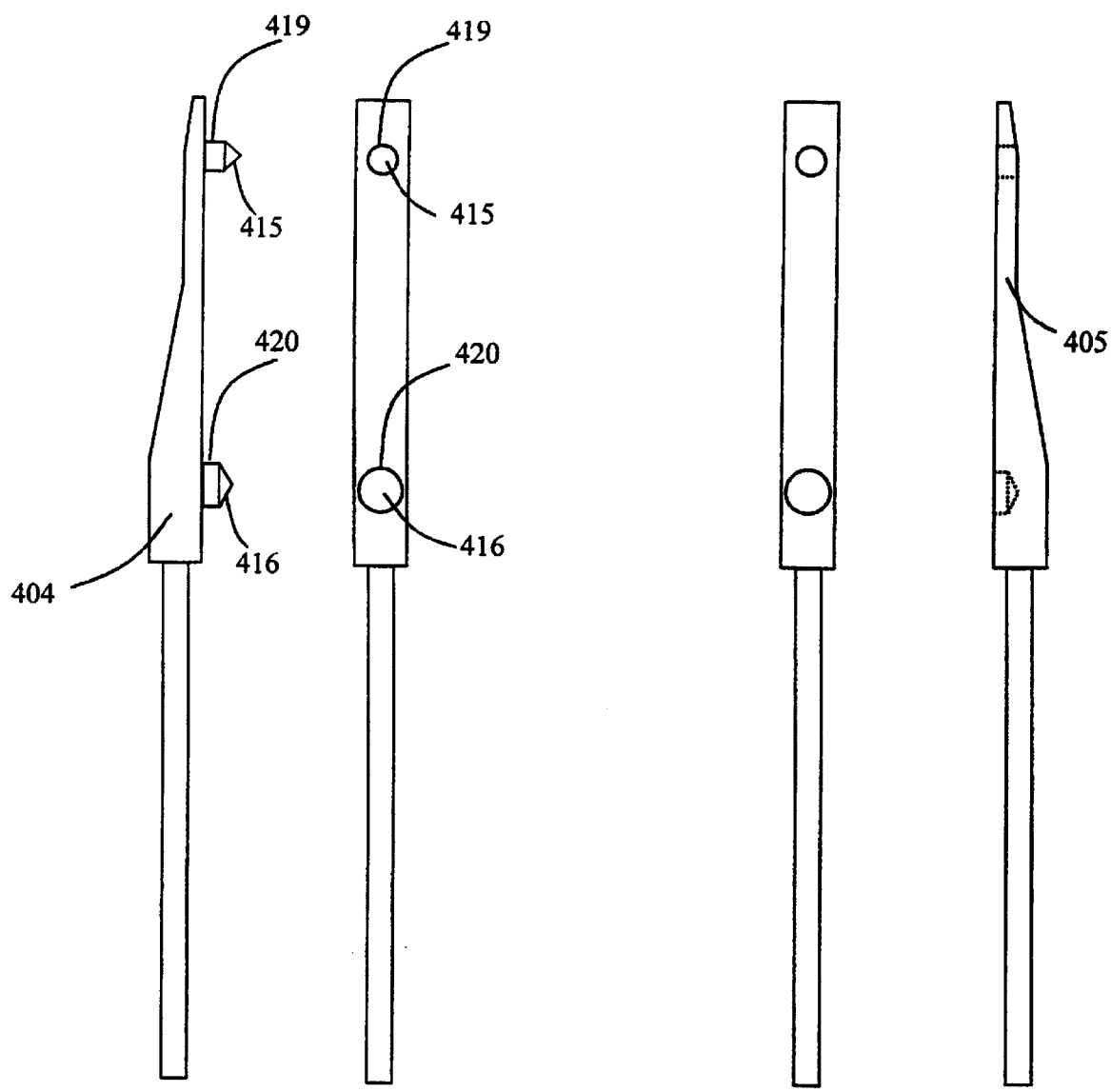
FIG. 12 is an alternative form of the clamping fingers.

Under some conditions of use, blood and other fluids may cause a blade to stick to one clamping finger as the fingers open. In FIG. 12, an alternative form of the clamping finger pins is illustrated. The alternative form of the pins is directed to assuring that a dull contaminated blade will always dislodge from the pins and drop from the scalpel clamping fingers when they open. The pin shapes as shown are specifically formed to secure the blade from any relative movement with respect to the clamping fingers when closed.

In FIG. 12, clamping finger 404 includes a conical topped pin 415 near the tip and a conical topped pin 416 near its base. Both conical topped pins 415 and 416 have cylindrical shoulders 419 and 420 which form lands that engage the slot 118 of a blade 106 (see FIG. 3). With the clamping fingers 404 and 405 closed, the blade 106 engages the shoulders 419 and 420 thereby preventing movement of the blade relative to the fingers.

When the clamping fingers 404 and 405 open, the blade 106 is restrained between guides 506A and 506B as further described below with reference to FIG. 16. The guides ensure separation and detachment of a dull blade from pins 415 and 416.

Figure 13:
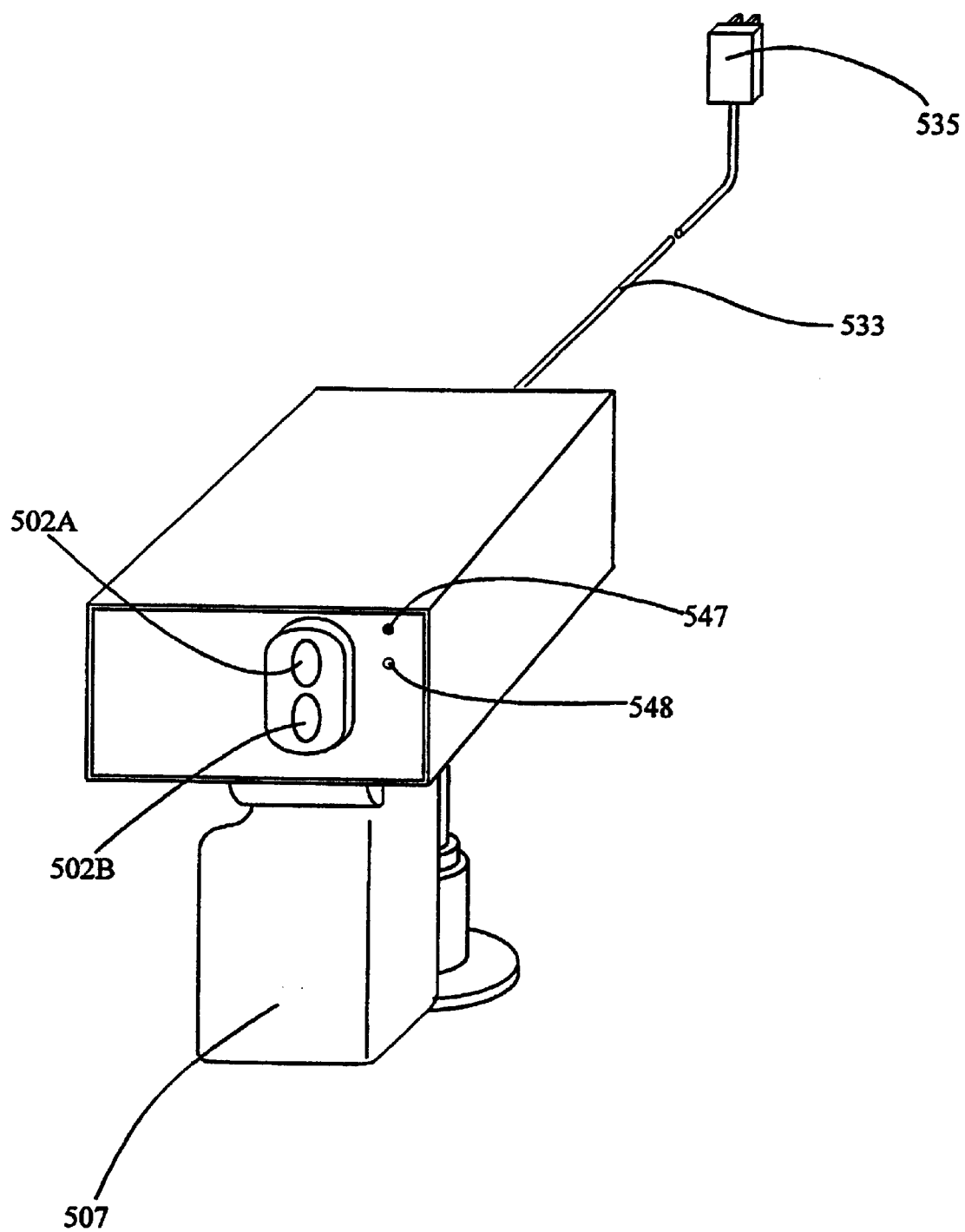
FIG. 13 is a perspective view of a dual blade exchange apparatus.

FIG. 13 depicts a dual blade exchange version of the apparatus. The positioning socket comprises two positioning sockets 502A and 502B in a vertical arrangement. The sockets 502A and 502B are identical to permit a scalpel to be inserted into either of the sockets. One sharps container 507 is situated below to collect spent blades regardless of which socket 502A and 502B is selected. The green 547 and yellow 548 lights perform the same "ready" or "in operation" function as above but for either socket 502A or 502B in the dual version of the apparatus.

In FIG. 13, the power cord 533 and plug 535 are depicted to emphasize that, as an alternative, the plug 535 may be an integral step down low voltage supply for the apparatus. In some environments, such as an operating room, a low voltage supply is desirable where electrically conductive fluids, such as ordinary water and blood, may be splashed during major surgery.

Internally, the dual version of the apparatus includes upper 520A and lower 520B cartridge boxes having cartridges 519A and 519B located therein. The cartridges 519A and 519B may be filled with identical blades, thus doubling the supply, or the blades in cartridge 519A may differ in size or style from the blades in cartridge 519B.

The cartridge boxes 520A and 520B are stacked as shown and fastened to a sliding table in turn fastened to a slider 521A for reciprocation in a channel 521B. The channel 521B in turn is mounted on a base 527 as above.

Also mounted on the base 527 are dual solenoids 525A and 525B. Each solenoid 525A or 525B is electrically coordinated with the two positioning sockets 502A or 502B to provide solenoidal actuation only for the socket into which a scalpel has been inserted. The solenoids 525A and 525B extend the plates 526A and 526B in coordination with the socket in use to extract a blade from either cartridge 519A or cartridge 519B. Although shown with two cartridge boxes 520A and 520B, the apparatus may be constructed three or more high in cartridge boxes 520 and solenoids 525.

Figure 14:
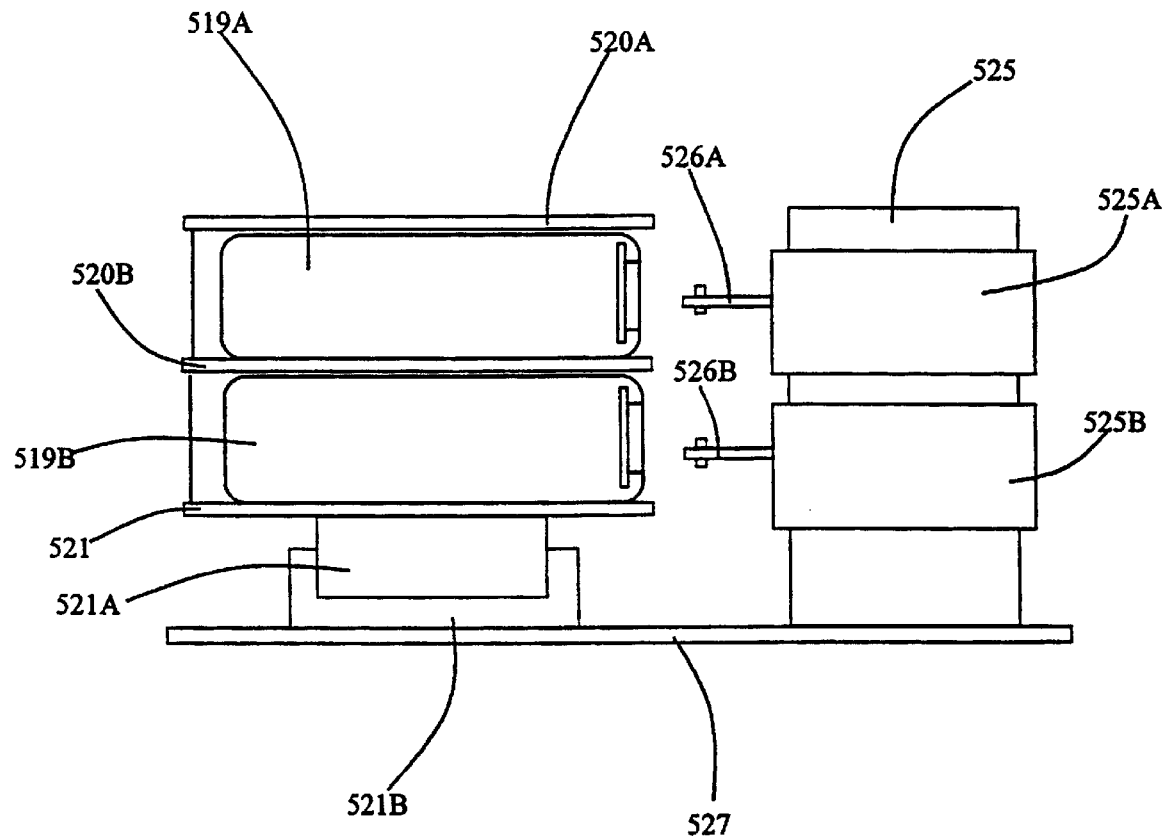
FIG. 14 is an internal view of the dual blade exchange apparatus of FIG. 13.

FIGS. 15A and 15B further depict in detail the alternate plates 526A and 526B of the dual version of the apparatus. Either plate 526A or 526B in FIG. 14 is affixed by any suitable fastening means at 545 to the corresponding solenoid plunger. The tip is insertable in the slot 118 of a blade 106 or 130 but limited to the thickness 537 of a blade by the stop 549 on the plate 526. The stop 549 contacts the blade 130 to prevent penetration further into the stack of blades 161 further in the cartridge.

Illustrated in FIGS. 16 and 17 is a detail of a device for assuring detachment of the spent blade 506 from the scalpel 501. Insertion of a scalpel frame into the upper 502A or lower 502B socket positions a small portion of the spent blade 506 between a pair of guides 506A and 506B adjacent the fingers 104 and 105. The guides 506A and 506B are fastened 503 to the dual socket 502. With insertion, twisting of the scalpel handle 111 causes fingers 104 and 105 to open and guides 506A and 506B assure the spent blade 506 is dislodged from the fingers and drops into sharps container 507.

What is claimed is:

1. Apparatus for exchanging blades in a scalpel comprising means for retaining the scalpel frame but permitting the scalpel fingers to open and release a scalpel blade therebetween, means to sense the open condition of the fingers, means to store and preposition at least one replacement blade, means to move the at least one replacement blade into position between the scalpel fingers in response to sensing of the open condition of the fingers, and means to externally indicate readiness for closure of the scalpel fingers.

2. The apparatus of claim 1 wherein the means for retaining a scalpel frame comprises a socket and means for preventing rotation of the frame in the socket.

3. The apparatus of claim 1 wherein the means to store and preposition at least one replacement blade comprises at least one cartridge capable of storing a plurality of replacement blades.

4. The apparatus of claim 3 wherein the means to move at least one replacement blade into position comprises means to reciprocate the cartridge and means to partially extract a replacement blade from the cartridge during reciprocation.

5. A method for exchanging blades in a scalpel without user contact of the blades comprising the steps of:

retaining the scalpel frame in a fixed position, moving a portion of the scalpel to cause the scalpel fingers to open thereby releasing a blade therein, in response to sensing the open condition of the scalpel fingers, providing a means for moving a replacement blade from a storage location to a location between the open scalpel fingers, moving a portion of the scalpel to cause the scalpel fingers to close thereby grasping the replacement blade, and removing the scalpel from the means retaining the scalpel frame in a fixed position.

6. The method of claim 5 including the step of partially extracting the replacement blade from the storage location, the storage location including a plurality of replacement blades.

7. The method of claim 5 including the steps of moving the storage location relative to the replacement blade to partially extract the replacement blade from a plurality of replacement blades in the storage location, and moving the storage location with the partially extracted replacement blade to position the replacement blade between the open scalpel fingers.

8. The method of claim 5 including the step of externally indicating the positioning of the replacement blade between the open scalpel fingers.

9. A method for exchanging blades in a scalpel without user contact of the blades comprising the steps of:

providing a means for moving a portion of the scalpel to open the scalpel and release a blade therein, in response to the open condition of the scalpel, providing a means for moving a replacement blade from a storage location to a location wherein the scalpel can close on the replacement blade for retention of the replacement blade, and moving said portion of the scalpel to close the scalpel on the replacement blade and thereby grasp the replacement blade.

10. The method of claim 9 wherein the storage location is a cartridge containing a plurality of replacement blades for automatic removal of a blade in response to the open condition of the scalpel.

11. The method of claim 9 including the step of indicating the open condition of the scalpel and a subsequent step of indicating complete closure of the scalpel.

* * * * *